US00PP12682P2

(12) United States Plant Patent
Polman

(10) Patent No.: US PP12,682 P2
(45) Date of Patent: Jun. 11, 2002

(54) SUTERA NAMED SUTTIS 98

(75) Inventor: Jacobus Gerardus Wilhelmus Polman, Tauge (NL)

(73) Assignee: Syngenta Seeds B.V., Westeinde (NL)

( * ) Notice: Subject to any disclaimer, the term of this patent is extended or adjusted under 35 U.S.C. 154(b) by 0 days.

(21) Appl. No.: 09/420,899

(22) Filed: Oct. 20, 1999

(51) Int. Cl.[7] ..... A01H 5/00
(52) U.S. Cl. ..... Plt./263
(58) Field of Search ..... Plt./263

(56) References Cited

PUBLICATIONS

UPOV–ROM GTITM Computer Database 2000/05, GTI JOUVE Retrieval Software, citation(s) for 'Suttis 98' Oct. 10, 2000.*

* cited by examiner

*Primary Examiner*—Bruce R. Campell
*Assistant Examiner*—Annette Para
(74) *Attorney, Agent, or Firm*—Edouard G. Lebel; Bruce Vrana

(57) ABSTRACT

A new Sutera plant particularly distinguished by its large white, round flower, early flowering, and a spreading, compact habit.

1 Drawing Sheet

BACKGROUND OF THE NEW PLANT

The present invention comprises a new distinct cultivar of Sutera, botanically known as *Sutera diffusa*. The new cultivar is propagated from cuttings resulting from the cross of 'A101' and 'A102'. 'A101' is a White flowering Sutera having a spreading habit. 'A101' is not commercially available and is not known by any synonyms. 'A102' is a White flowering Sutera having a larger than normal flower. 'A102' is not commercially available and is not known by any synonyms. Neither 'A101' or 'A102' has been patented. As a result of this cross the present cultivar was created in 1996 in Enkhuizen, Netherlands and has been repeatedly asexually reproduced by cuttings in Enkhuizen, Netherlands and Sarrians, France over a three year period. It has been found to retain its distinctive characteristics through successive propagations, and this novelty appears to be firmly fixed.

This new Sutera plant is an annual in most climatical zones in the U.S., only in zones 8, 9 and 10 it is a perennial plant.

DESCRIPTION OF THE DRAWING

This new Sutera plant is illustrated by the accompanying photographic drawing which shows blooms, buds and foliage of the plant in full color, the color shown being as true as can be reasonably obtained by conventional photographic procedures.

DESCRIPTION OF THE NEW CULTIVAR

The following detailed descriptions set forth the distinctive characteristics of this new Sutera. The data which defines these characteristics were collected from asexual reproductions carried out in Enkhuizen, Netherlands. The plant history was taken on 15 weeks old plants, blossomed under natural light in a greenhouse. Color readings were taken in the greenhouse under ambient light. Color references are primarily to the R.H.S. Colour Chart of The Royal Horticultural Society of London.

The Plant

Classification — Botanical: *Sutera diffusa.*
Parentage:
- *Female parent.*—A seedling named 'A101' is one of our seedlings from our A-generation of plants bred in 1995.
- *Follen parent.*—A seedling named 'A102' is one of our seedlings from our A-generation of plants bred in 1995.

Growth habit: Spreading.
Plant height: 8–15 cm.
Spreading area of plant: 30–40 cm.
Growth rate: Rapid growing.
Strength: Good.
Branching habit: Short internodes and on each knot more than two appearing shoots give a plant that is more branched than normal.
Blooming period: From May till November.

The Stem

Diameter: 1–2 mm.
Shape: Cylindrical.
Anthocyan pigmentation: Absent.
Color of the stem: R.H.S. color chart 137B.
Length of internode: 10–30 mm, depending on the light where the plant is propagated.
Pubescence: Sparse.

The Foliage

Phyllotaxis: Opposite.
Shape of blade: Heart-shaped (Cordate).
Shape of blade base: Heart-shaped (Cordate).
Shape of blade tip: Blunt (truncate).
Leaf margin: Toothed (dentate).
Texture: Smooth, young leaves a bit hairy.
Length: 10–20 mm.
Width: 15–25 mm.
Depth of incision: 1–2 mm.
Color:
- *Upper side.*—Dark green 137B.
- *Lower side.*—Light green 136C.

Pubescence: Sparse, only on the upper side.
Length of petiole: 10–20 mm.
Diameter of petiole: 2 mm.
Color of petiole: Dark green 137B.

The Bud

Pedicel length: 8–20 mm, depending on season.
Size:
*Diameter.*—2 mm.
*Length.*—4–8 mm.
Shape: Elongated.
Color: Medium green 137C.
Sepals:
*Colour.*—Medium green 137C.
*Shape.*—Erect calyx.
*Number.*—5.
*Size.*—2 mm.

The Flower

Direction: Ascending.
Outward curvation of petal: Medium curved.
Diameter: 10–15 mm.
Height: 12–18 mm.
Form: Salverform.
Symmetry: Radial symmetric.
Type: Solitary.
Color: White 155 D.
Corolla tube: Cylindrical.
Overlapping of petals: Separate.
No. of petals: 5.
Shape of the petals: Gamopetalous, grown together at the base of the petal, forming a corolla.
Size of the petal:
*Length.*—3–6 mm.
*Width.*—3–6 mm.
Petalform: Single.
Calyx: Length of 8–10 mm.
Anthocyan pigmentation of Calyx limb: Absent.
Fragrance: No fragrance.
Lastingness of flower: Flowers stay open 8–10 days.

Reproductive Organs

Number of reproductive organs: 1 pistil, 4 stamens.
Pollen production: Very low.
Stigma color: Light green 138D.
Stamen color: Yellow 13A.
Stamen arrangement: Didynamous.
Stamen type: Basifixed.
Dehiscence of stamens: Extrorse.
Ovary position: Ovary superior, flower hypogynous.
Style shape: Style terete.

Seeds

Only few seeds are formed, almost sterile plant.

Few seeds that occur are light yellow 13 C, small, round, diameter approx. 0.1 mm.

Roots

Type of roots: Fibrous. Roots start to grow at the nodes that contact the soil.

Physiological and ecological characteristics.

Good tolerance to heat and cold.

High resistance to lice and whitefly.

High resistance to mildew.

Propagation

Propagation is done by cuttings.

Tips of stems are used, which takes 4 days to initiate roots and 10 days to develop roots.

Difference from patents and comparison

| | 'Suttis 98' | 'A101' | 'A102' | Giant Snowflake |
|---|---|---|---|---|
| petal length | short | long | short | long |
| pedal width | broad | broad | narrow | narrow |
| internodes | short | long | short | long |
| size of flower | large | large | small | large |

What is claimed is:

1. A new and distinct variety of Sutera plant, substantially as herein illustrated and described, characterized particularly as to novelty by larger White flowers than other Sutera plants, and a growing habit that is first compact, spreading and hanging.

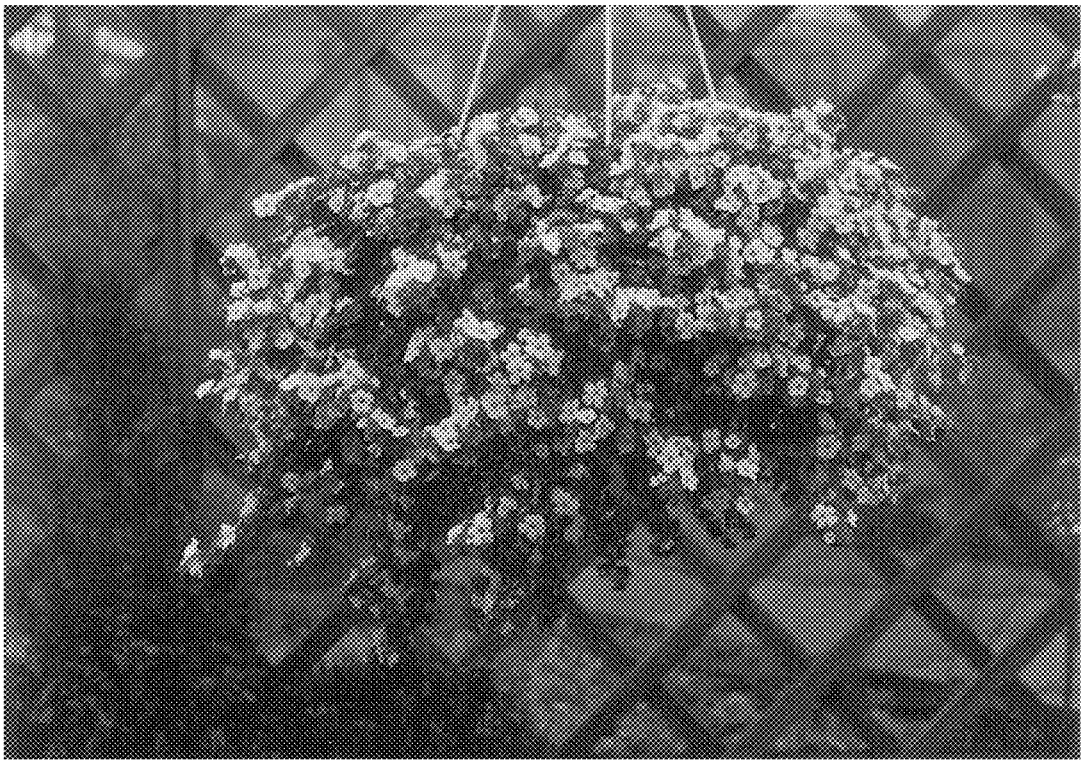

* * * * *